(12) United States Patent
Albeck et al.

(10) Patent No.: US 7,652,065 B2
(45) Date of Patent: Jan. 26, 2010

(54) TELLURIUM COMPOUNDS AND THEIR USE AS IMMUNOMODULATORS

(75) Inventors: Michael Albeck, Ramat-Gan (IL); Benjamin Sredni, Kfar-Saba (IL)

(73) Assignee: BioMAS Ltd., Kfar-Saba (IL)

( * ) Notice: Subject to any disclaimer, the term of this patent is extended or adjusted under 35 U.S.C. 154(b) by 71 days.

(21) Appl. No.: 11/663,031

(22) PCT Filed: Sep. 15, 2005

(86) PCT No.: PCT/IL2005/000989

§ 371 (c)(1),
(2), (4) Date: Mar. 16, 2007

(87) PCT Pub. No.: WO2006/030437

PCT Pub. Date: Mar. 23, 2006

(65) Prior Publication Data

US 2008/0015175 A1    Jan. 17, 2008

Related U.S. Application Data

(60) Provisional application No. 60/610,660, filed on Sep. 17, 2004.

(51) Int. Cl.
A01N 43/26 (2006.01)
A61K 31/335 (2006.01)
C07D 317/70 (2006.01)

(52) U.S. Cl. ...................... 514/463; 549/432
(58) Field of Classification Search ............ None
See application file for complete search history.

(56) References Cited

U.S. PATENT DOCUMENTS

| | | |
|---|---|---|
| 3,369,550 A | 2/1968 | Armao |
| 4,752,614 A | 6/1988 | Albeck et al. |
| 4,761,490 A | 8/1988 | Albeck et al. |
| 4,929,739 A | 5/1990 | Sredni et al. |
| 4,962,207 A | 10/1990 | Albeck et al. |
| 5,093,135 A | 3/1992 | Albeck et al. |
| 5,102,908 A | 4/1992 | Albeck et al. |
| 5,262,149 A | 11/1993 | Sredni et al. |
| 5,271,925 A | 12/1993 | Sredni et al. |
| 5,576,347 A | 11/1996 | Sredni et al. |
| 5,654,328 A | 8/1997 | Sredni et al. |
| 6,428,534 B1 | 8/2002 | Joye et al. |
| 6,472,381 B1 | 10/2002 | Albeck et al. |
| 6,552,089 B1 | 4/2003 | Sredni et al. |
| 6,747,008 B1 | 6/2004 | Rodgers et al. |
| 2003/0148970 A1 | 8/2003 | Besterman et al. |
| 2006/0063750 A1 | 3/2006 | Sredni et al. |
| 2008/0260770 A1 | 10/2008 | Sredni et al. |

FOREIGN PATENT DOCUMENTS

| | | |
|---|---|---|
| DE | 4007473 | 9/1991 |
| EP | 0583026 | 2/1994 |
| EP | 583026 | 4/1997 |
| GB | 1427415 | 3/1976 |
| WO | WO 96/06618 | 3/1996 |
| WO | WO 96/18392 | 6/1996 |
| WO | WO 96/18401 | 6/1996 |
| WO | WO 01/98325 | 12/2001 |
| WO | WO 03/044038 | 5/2003 |
| WO | WO 2005/060341 | 7/2005 |
| WO | WO 2006/030437 | 3/2006 |
| WO | WO 2006/030438 | 3/2006 |
| WO | WO 2006/030439 | 3/2006 |
| WO | WO 2006/030440 | 3/2006 |

OTHER PUBLICATIONS

Dumont Expert Opinion in Therapeutic Patents, 2006, 16(7), 879-912.*
"Human Immunodeficiency Infection", http://merck.com/mmhe/sec17/ch199/ch199a.html, accessed May 19, 2008.*
"IUPAC gold books—acyl groups", http://goldbook.iupac.org/A00123.html, accessed Nov. 27, 2007.*
Gross et al. "Tellurium Dioxide Suspension in the Treatment of Seborrhea Capitis", A.M.A. Archives of Dermatology, 78(1): 92-94, 1958.
Jimenez et al. "Interleukin 1 Protects From Cytosine Arabinoside-Induced Alopecia in the Rat Model", esearch Communications, The FASEB Journal, 5: 2456-2458, 1991.
Kalechman et al. "Anti-IL-10 Therapeutic Strategy Using the Immunomodulator AS101 in Protecting Mice From Sepsis-Induced Death: Dependence on Timing of Immunomodulating Intervention", The Journal of Immunology, 169(1): 384-392, 2002.
Kalechman et al. "Inhibition of Interleukin-10 by the Immunomodulator AS101 Reduces Mesangial Cell Proliferation in Experimental Mesangioproliferative Glomerulonephritis", The Journal of Biological Chemistry, 279(23): 24724-24732, 2004.
Makarovsky et al. "Tellurium Compound AS101 Induces PC12 Differentiation and Rescue the Neurons From Apoptotic Death", Annals of the New York Academy of Sciences, 1010: 659-666, 2003.
Shohat et al. "In Vitro Cytokine Profile in Childhood Alopecia Areata and the Immunomodulatory Effects of AS-101", Clinical and Experimental Dematology, 30(4): 432-434, 2005.
Sishi et al. "Defective Production of Interleukin-2 (IL-2) in Patients with Alopecia Areata", Chemical Abstracts, 108: 519, 1988, Abstract.
Sredni et al. "Hair Growth Induction by the Tellurium Immunomodulator AS101: Association With Delayed Terminal Differentiation of follicular Keratinocytes and Ras-Dependent Up-Regulation of KGF Expression", The FASEB Journal, 18(2): 400-402, 2004.
Sredni et al. "The Protective Role of the Immunomodulator AS101 Against Chemotherapy-Induced Alopecia Studies on Human and Animal Models", International Journal of Cancer, 65(1): 97-103, 1996.

(Continued)

*Primary Examiner*—James O Wilson
*Assistant Examiner*—Noble Jarrell (57) ABSTRACT

Novel tellurium-containing compounds and uses thereof as immunomodulators are disclosed.

6 Claims, 5 Drawing Sheets

OTHER PUBLICATIONS

Siderowf et al. "Update on Parkinson Disease", Annals of Internal Medicine, 138(8): 651-658, 2003.
Black et al. "Activation of Interleukin-1β by a Co-Induced Protease", FEBS Letters, 247(2): 386-390, 1989.
Hara et al. "Inhibition of Interleukin 1β Converting Enzyme Family Proteases Reduces Ischemic and Excitotoxic Neuronal Damage", Proc. Natl. Acad. Sci. USA, 94: 2007-2012, 1997.
Hardy "The Secret Life of the Hair Follicle", Trends in Genetics, 8(2): 41-78, 1992.
Kalechman et al. "Up-Regulation by Ammonium Trichloro(Dioxoethylene-0,0') Tellurate (AS101) of Fas/Apo-1 Expression on B16 Melanoma Cells: Implications for the Antitumor Effects of AS101", The Journal of Immunology, 161: 3536-3542, 1998.
Sredni et al. "Bone Marrow-Sparing and Prevention of Alopecia by AS101 in Non-Small-Cell Lung Cancer Patients Treated With Carboplatin and Etoside", Journal of Clinical Oncology, 13(9): 2342-2353, 1995.
Wieslander et al. "Antioxidative Properties of Organotellurium Compounds in Cell Systems", Biochemical Pharmacology, 55: 573-584, 1998.
Communication Pursuant to Rules 109 and 110 EPC Dated Nov. 20, 2006 From the European Patent Office Re.: Application No. 04801399.9.
Examination Report Dated Oct. 29, 2008 From the Government of India, Patent Office Re.: Application No. 2606/CHENP/2006.
International Preliminary Report on Patentability Dated Apr. 26, 2007 From the International Bureau of WIPO Re.: Application No. PCT/IL2005/000991.
International Preliminary Report on Patentability Dated Sep. 28, 2006 From the International Bureau of WIPO Re.: Application No. PCT/IB2004/004163.
International Preliminary Report on Patentability Dated Mar. 29, 2007 From the International Bureau of WIPO Re.: Application No. PCT/IL2005/000989.
International Preliminary Report on Patentability Dated Mar. 29, 2007 From the International Bureau of WIPO Re.: application No. PCT/IL2005/000990.
International Preliminary Report on Patentability Dated Mar. 29, 2007 From the International Bureau of WIPO Re.: Application No. PCT/I12005/000992.
Official Action Dated Nov. 7, 2008 From the US Patent and Trademark Office Re.: U.S. Appl. No. 11/226,374.
Official Action Dated Jan. 11, 2008 From the US Patent and Trademark Office Re.: U.S. Appl. No. 11/226,374.
Official Action Dated Feb. 14, 2007 From the US Patent and Trademark Office Re.: U.S. Appl. No. 11/226,374.
Official Action Dated May 14, 2008 From the US Patent and Trademark Office Re.: U.S. Appl. No. 11/663,032.
Official Action Dated Aug. 26, 2008 From the Canadian Intellectual Property Office Re.: Application No. 2,550,459.
Official Action Dated Oct. 27, 2008 From the US Patent and Trademark Office Re.: U.S. Appl. No. 11/663,032.
Boettner et al. "the Role of Rho GTPase in Disease Development", Gene, 286: 155-174, 2002.
Delagarza "Pharmacologic Treatment of Alzheimer's Desease: An Update", American Family Physician, 68(7): 1365-1372, Oct. 1, 2003.
Shults "Treatments of Parkinson Disease. Circa 2003", Archives of Neurology, 60: 1680-1684, Dec. 2003.

* cited by examiner

TELLURIUM COMPOUNDS AND THEIR USE AS IMMUNOMODULATORS

RELATED APPLICATIONS

This Application is a National Phase of PCT Patent Application No. PCT/IL2005/000989 having International Filing Date of Sep. 15, 2005, which claims the benefit of U.S. Provisional Patent Application No. 60/610,660 filed on Sep. 17, 2004. The contents of the above Applications are all incorporated herein by reference.

FIELD AND BACKGROUND OF THE INVENTION

The present invention relates to novel tellurium-containing compounds, compositions comprising such compounds, and their use as immunomodulators.

Cytokines play an important role in a regulation of the immune system. Several studies indicate that variations in cytokine expression are associated with disease activity in immune mediated or inflammatory disorders, including autoimmune disorders (*Acta. Univ. Palacki. Olomuc., Fac. Med.* 143: 19-29, 2000; *Rheumatol.* 39: 1078, 2000; *J. Immunol* 167: 5338, 2001), trauma (surgery) (*Blood* 87: 2095-2147, 1996), ischemic diseases (myocardial infarction) (*Acta. Univ. Palacki. Olomuc., Fac. Med.* 143: 19-29, 2000; *Cell. Immunol* 184: 12, 1998), Alzheimer's disease (*Blood* 87: 2095-2147, 1996), liver diseases (*Immunol. Rev.* 174: 192-209, 2000), rheumatoid arthritis (*Arthritis Rheum.* 44: 275, 2001; *J. Rheumatol.* 28: 1779, 2001), obesity (*Shock* 14: 253, 2000), psoriasis (*Arch. Dermatol. Res.* 293: 334, 2001), and sepsis (*Acta. Univ. Palacki. Olomuc., Fac. Med.* 143: 19-29, 2000; *Blood* 87: 2095-2147, 1996; *Shock* 16: 441, 2000; *J. Med.* 31: 15, 2000).

IL-1β is crucial for the induction of fever and acute-phase response during local tissue damage; in systemic inflammation it contributes to inflammatory reaction (*Acta. Univ. Palacki. Olomuc., Fac. Med.* 143: 19-29, 2000). This cytokine is important in response to tissue damage and infection, but is not required for normal development and homeostasis. Serum levels of IL-1β and IL-1 Ra are significantly elevated in severe sepsis (*Acta. Univ. Palacki. Olomuc., Fac. Med.* 143: 19-29, 2000).

The IL-1 family of cytokines, which include IL-18 and IL-1β are key hormones of the immune system. Both IL-18 and IL-1β are expressed and produced by various types of cells from hematopoetic and nonhematopoetic lineages, such as dendritic cells, monocytes/macrophages, microglia cells, keratinocytes, intestinal epithelial cells, etc. Recent studies emphasize the pathophysiological role of IL-18 and IL-1β in a variety of neurodegenerative, autoimmune and inflammatory diseases, such as inflammation, hemaopoiesis and wound healing (*Immunol. Today* 7: 45-56, 1986).

Interleukin-18 is an early signal in the development of T-lymphocyte helper type 1 (Th1) responses. It acts together with IL-12 to induce various cytokines, including IFN-γ, to activate Th1 cells. IFN-γ is in turn responsible for inducing production of the soluble receptor protein, IL-18 binding protein (IL-18BP), a native down-regulator of IL-18 activity, which specifically binds IL-18 and neutralizes its biological activity in vitro and in vivo (*Immunity* 10: 127, 1999).

IL-18 and IL-1β are expressed and produced in an inactive form, which requires activation by protease enzymes. The protease enzymes are divided into four families, (serine-, metallo-, aspartic- and cysteine-proteases) based on their catalytic residues and mechanism of action. Whereas serine proteases utilize a nucleophilic hydroxyl of the serine residue and aspartic and metalloproteases posses carboxylates as active functionalities, the cysteine proteases have an active-site thiol-nucleophile.

The caspase enzymes (Cysteine Aspartic-Specific Proteases) are a family of intracellular cysteine endopepetidases, which cleave their substrates after aspartate residues (*Ann. Rev. Immunol.* 17: 781-828, 1999). The caspases are divided into two classes, based on the lengths of their N-terminal prodomains. Caspases-1,-2,-4,-5,-8, and -10 have long prodomains; and caspases-3,-6,-7, and -9 have short prodomains.

Caspase 1, which is also known and referred to herein, interchangeably, as interleukin-β-converting enzyme (ICE), is expressed as a proenzyme of 45 kD in many tissues (*J. Clin. Immunol* 19:1, 1999). Upon stimulation, it undergoes activation by proteolytic cleavage. Active ICE is a tetramer of two non-identical subunits p10 and p20 in 2:2 proportion, which is uniquely responsible for cleaving pro-interleukin-1β (31 or 33 kD), into mature interleukin-1β (IL-1β)(17.5 kD), which consists of the C-terminal 153 residues of the inactive form; and pro-IL-18 (24 kD), which is cleaved at Asp35, into the biologically active 18 kD form (*J. Immunother.* 25: S4-S11, 2002; *Nature* 386: 619, 1997; *Science* 275: 206, 1997). The active cytokine is then released by a non-standard mechanism, since unlike the case with most secretory proteins, the precursor lacks a signal sequence and is not associated with membrane-bound compartments (*J. Exp. Med.* 167: 389-407, 1988).

ICE therefore plays an important role in physiological processes mediated by IL-1β and IL-18.

Various tellurium compounds, having immunomodulating properties, have been shown to have beneficial effects in diverse preclinical and clinical studies. A particularly effective family of tellurium-containing compounds is taught, for example, in U.S. Pat. Nos. 4,752,614; 4,761,490; 4,764,461 and 4,929,739. The immunomodulating properties of this family of tellurium-containing compounds is described, for example, in U.S. Pat. Nos. 4,962,207, 5,093,135, 5,102,908 and 5,213,899, which are all incorporated by reference as if fully set forth herein.

One of the most promising compounds described in these patents is ammonium trichloro(dioxyethylene-O,O')tellurate, which is also referred to herein and in the art as AS101. AS101, as a representative example of the family of tellurium-containing compound discussed hereinabove, exhibits antiviral (*Nat. Immun. Cell Growth Regul.* 7(3):163-8, 1988; *AIDS Res Hum Retroviruses.* 8(5):613-23, 1992), and tumoricidal activity (*Nature* 330(6144):173-6, 1987; *J. Clin. Oncol.* 13(9):2342-53, 1995; *J. Immunol.* 161(7):3536-42, 1998.

It has been suggested that AS101, as well as other tellurium-containing immunomodulators, stimulate the innate and acquired arm of the immune response. For example, it has been shown that AS101 is a potent activator of interferon (IFN) (IFN) in mice (*J. Natl. Cancer Inst.* 88(18):1276-84, 1996) and humans (*Nat. Immun. Cell Growth Regul.* 9(3): 182-90, 1990; *Immunology* 70(4):473-7, 1990; *J. Natl. Cancer Inst.* 88(18):1276-84, 1996.)

It has also been demonstrated that AS101, as well as other tellurium-containing immunomodulators, induce the secretion of a spectrum of cytokines, such as IL-1α, IL-6 and TNF-α, and that macrophages are one main target for AS101 (*Exp. Hematol.* 23(13):1358-66, 1995) and it was found to inhibit IL-10 at the m-RNA level, and this inhibition may cause an increase in IL-12 (*Cell Immunol.* 176(2):180-5, 1997); *J. Natl. Cancer Inst.* 88(18):1276-84, 1996).

Other publications describing the immunomodulation properties of AS101 include, for example, "The immunomodulator AS101 restores T(H1) type of response suppressed by *Babesia rodhaini* in BALB/c mice". *Cell Immunol* 1998 February; "Predominance of TH1 response in tumor-bearing mice and cancer patients treated with AS101 ". *J Natl Cancer Inst* 1996 September; "AS-101: a modulator of in vitro T-cell proliferation". *Anticancer Drugs* 1993 June; "The immunomodulator AS101 administered orally as a chemoprotective and radioprotective agent". *Int J Immunopharmacol* 1992 May; "Inhibition of the reverse transcriptase activity and replication of human immunodeficiency virus type 1 by AS101 in vitro". *AIDS Res Hum Retroviruses* 1992 May; "Immunomodulatory effects of AS101 on interleukin-2 production and T-lymphocyte function of lymphocytes treated with psoralens and ultraviolet A". *Photodermatol Photoimmunol Photomed* 1992 February; "Use and mechanism of action of AS101 in protecting bone marrow colony forming units-granulocyte-macrophage following purging with ASTA-Z 7557 ". *Cancer Res* 1991 Oct. 15; "The effect of the immunomodulator agent AS101 on interleukin-10 production in systemic lupus erythematosus (SLE) induced in mice by a pathogenic anti-DNA antibody". *Clin Exp Immunol* 1990 March; "Toxicity study in rats of a tellurium based immunomodulating drug, AS-101: a potential drug for AIDS and cancer patients". *Arch Toxicol* 1989; "The biological activity and immunotherapeutic properties of AS-101, a synthetic organotellurium compound". *Nat Immun Cell Growth Regul* 1988; and "A new immunomodulating compound (AS-101) with potential therapeutic application". *Nature* 1987 Nov.

In addition to its immunomodulatory effect, AS101 is also characterized by low toxicity. Toxicity tests have shown that LD50 values in rats following intravenous and intramuscular administration of AS101 are 500-1000 folds higher than the immunologically effective dose.

While AS101 and its immunomodulating properties has been studied, bis-tellurium compounds and their properties have never been suggested nor practiced hitherto.

There is thus a widely recognized need for and it would be highly advantageous to have novel compounds, which are characterized as non toxic and which can be utilized in the treatment of medical conditions such as those delineated above.

SUMMARY OF THE INVENTION

The present invention provides novel bis-tellurium compounds, compositions comprising these compounds, and uses thereof.

The compounds of the present invention have the general Formula I:

Formula I wherein:
each of m and n is independently an integer from 0 to 3; and
each of $R_1$-$R_8$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido.

Preferably, n and m are each 0. More preferably, each of $R_1$, $R_4$, $R_5$ and $R_8$ is hydrogen. The preferred compound according to this embodiment is referred to hereinafter as SAS.

According to further features in the described preferred embodiments, the compound of formula I may be used in the treatment or prevention of a condition in which inhibition of interleukin-1β-converting enzyme is beneficial.

According to still further features in the described preferred embodiments, the compound of formula I may be used in the preparation of a medicament for the treatment or prevention of a condition in which inhibition of interleukin-1β-converting enzyme is beneficial.

The conditions which may be treated or prevented by the compound of formula I include, without limitation, an IL-1 mediated disease, an inflammatory disease (such as, for example, septic shock, septicemia, adult respiratory distress syndrome, arthritis, cholangitis, colitis, encephalitis, hepatitis, pancreatitis and reperfusion injury), an autoimmune disease (such as, for example, psoriasis, rheumatoid arthritis, systemic lupus erythematosus, scleroderma, chronic thyroiditis, Graves' disease, autoimmune gastritis, insulin-dependent diabetes mellitus, autoimmune hemolytic anemia, autoimmune neutropenia, throbocytopenia, chronic active hepatitis, myasthenia gravis and multiple sclerosis), an ischemic disease (such as, for example, cerebral ischemia, myocardial ischemia, myocardial infarction, stroke, ischemic kidney disease; an immune based diseases, and hypersensitivity), a destructive bone disorder, a proliferative disorder, an infectious disease, a neurodegenerative disease (such as, for example, amyotrophic lateral sclerosis, Alzheimer's disease, Parkinson's disease, primary lateral sclerosis, or trauma, such as spinal cord injury), a disease associated with cell death, an excess dietary alcohol intake disease, retinal disorders, uveitis, inflammatory peritonitis, osteoarthritis, pancreatitis, asthma, glomerulonephritis, diabetes, inflammatory bowel disease, Crohn's disease, atopic dermatitis, scarring, graft vs host disease, organ transplant rejection, organ apoptosis after burn injury, osteoporosis, leukemia and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, burns, Shigellosis, Huntington's disease, Kennedy's disease, prion disease, epilepsy, acute and chronic heart disease, myocardial infarction, congestive heart failure, atherosclerosis, coronary artery bypass graft, spinal muscular atrophy, HUV-related encephalitis, aging, neurological damage due to stroke, traumatic brain injury, spinal cord injury, yellow fever, dengue fever, Japanese encephalitis, liver disease, renal disease, polycystic kidney disease, *H. pylori*-associated gastric and duodenal ulcer disease, HIV infection, tuberculosis, an immunotherapy for the treatment of various forms of cancer, organ failure, meningitis, obesity and related diseases, diabetes, hyperglycemia, hyperinsulinemia and a complication associated with coronary artery bypass grafts.

According to still further features in the described preferred embodiments, the compound of formula I may be used in treating or preventing obesity and related disorders, by administering to a subject in need thereof a therapeutically effective amount. The route of administration may be, for example, by the oral, parenteral, rectal, nasal, topical and inhalation routes.

Oral administration may optionally and preferably comprise a dose of from about 0.1 mg to about 200 mg per day, preferably of from about 1 mg to about 100 mg per day. A therapeutically effective amount of said compound ranges from about 0.02 mg/m$^2$/day to about 40 mg/m$^2$/day.

The tellurium-containing compound may optionally form a part of a pharmaceutical composition, further comprising a pharmaceutically acceptable carrier. For topical administration, the concentration of tellurium-containing compound in the carrier optionally and preferably comprises from about 0.01 weight percentages to about 50 weight percentages.

The carrier may optionally further comprise an additional active agent, such as, for example, an antibiotic agent, an anti-diabetic agent, an antihyperglemic agent, an antimicrobial agent, an anti-obesity agent, an anesthetic agent, an antioxidant, a chemotherapeutic agent, an antidepressant, an antihistamine, a vitamin, and a hormone.

As used herein, the term "about" refers to ±10%.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF THE INVENTION

The present invention is of novel tellurium-containing compounds and, more particularly, of novel bis-tellurium compounds, which can be beneficially used in various therapeutic applications such as, but not limited to treatment of an interleukin-1β-converting enzyme-mediated condition, an IL-1 mediated disease, an inflammatory disease, an autoimmune disease, an ischemic disease, a destructive bone disorder, a proliferative disorder, an infectious disease, a neurodegenerative disease, a disease associated with cell death, diabetes and obesity and related diseases.

The principles and operation of the compositions and methods according to the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed in the Background section hereinabove, various tellurium-containing compounds, which exhibited a variety of advantageous immunomodulating properties have been described in the art.

The present inventors have now designed and successfully prepared and practiced a novel family of tellurium-containing compounds. As is demonstrated in the Examples section that follows, these compounds were tested and found highly active as immunomodulators which, for example, can interfere with the activity of some key enzymes.

The compounds presented herein are collectively represented by the general Formula I:

Formula I wherein:

each of m and n is independently an integer from 0 to 3; and each of $R_1$-$R_8$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, carbonyl, alkylcarbonylalkyl, carboxyalkyl, acyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfonamido.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms. The alkyl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, sulfonamide, phosphonyl, phosphinyl, carbonyl, thiocarbonyl, carboxy, thiocarboxy, carbamate, thiocarbamate, amido, sulfonamido, and amino, as these terms are defined herein.

As used herein, the term "hydroxyalkyl" refers to an alkyl, as this term is defined herein, substituted by a hydroxy group, as defined herein, and includes, for example, hydroxymethyl, hydroxyethyl, hydroxypropyl and hydroxy-n-butyl.

As used herein, the term "halogen", which is also referred to herein interchangeably as "a halogen atom" or "halo", includes chloro (Cl), bromo (Br), iodo (I) and fluoro (F).

The term "haloalkyl" refers to an alkyl, as this term is defined herein, substituted by a halogen, as defined herein, and includes, for example, chloromethyl, 2-iodoethyl, 4-bromo-n-butyl, iodoethyl, 4-bromo-n-pentyl and the like.

The term "alkanoyloxy" refers to a carbonyl group, as define herein and includes, for example, acetyl, propionyl, butanoyl and the like.

The term "carboxyalkyl" refers to an alkyl, as this term is defined herein, substituted by a carboxy group, as defined herein, and includes, for example, carboxymethyl, carboxyethyl, ethylenecarboxy and the like.

The term "alkylcarbonylalkyl" refers to an alkyl, as this term is defined herein, substituted by a carbonyl group, as defined herein, and includes, for example, methanoylmethyl, ethanoylethyl and the like.

The term "amidoalkyl" refers to an alkyl, as this term is defined herein, substituted by an amide group, as defined herein, and includes, for example, —CH$_2$CONH$_2$; —CH$_2$CH$_2$CONH$_2$; —CH$_2$CH$_2$CH$_2$CONH$_2$ and the like.

The term "cyanoalkyl" refers to an alkyl, as this term is defined herein, substituted by an cyano group, as defined herein, and includes, for example, —CH$_2$CN; —CH$_2$CH$_2$CN; —CH$_2$CH$_2$CH$_2$CN and the like.

The term "N-monoalkylamidoalkyl" refers to an alkyl, as this term is defined herein, substituted by an amide group, as defined herein, in which one of R' and R" is an alkyl, and includes, for example, —CH$_2$CH$_2$CONHCH$_3$, and —CH$_2$CONHCH$_2$CH$_3$.

The term N,N-dialkylamidoalkyl refers to an alkyl, as this term is defined herein, substituted by an amide group, as defined herein, in which both R' and R" are alkyl, and includes, for example, —CH$_2$CON(CH$_3$)$_2$; CH$_2$CH$_2$CON(CH$_2$—CH$_3$)$_2$ and the like.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, phosphonyl, phosphinyl, carbonyl, thiocarbonyl, carboxy, thiocarboxy, carbamate, thiocarbamate, amido, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, sulfate, cyano, nitro, phosphonyl, phosphinyl, phosphonium, carbonyl, thiocarbonyl, carboxy, thiocarboxy, carbamate, thiocarbamate, amido, sulfonamido, and amino, as these terms are defined herein. Representative examples are piperidine, piperazine, tetrahydro furane, tetrahydropyrane, morpholino and the like.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is hydrogen, alkyl, alkenyl, cycloalkyl, aryl, heteroaryl (bonded through a ring carbon) or heteroalicyclic (bonded through a ring carbon) as defined herein.

A "thiocarbonyl" group refers to a —C(=S)—R' group, where R' is as defined herein for R'.

A "carboxy" group refers to a —C(=O)—O—R' or a —O—C(=O)—R' group, where R' is as defined herein.

A "sulfinyl" group refers to an —S(=O)—R' group, where R' is as defined herein.

A "sulfonyl" group refers to an —S(=O)$_2$—R' group, where R' is as defined herein.

A "sulfate" group refers to a —O—S(=O)$_2$—OR' group, where R' is as defined herein.

A "sulfonamido" group refers to a —S(=O)$_2$—NR'R" group or a R'S(=O)$_2$—NR", with R' is as defined herein and R" is as defined for R'.

A "carbamyl" or "carbamate" group refers to an —OC(=O)—NR'R" group or a R"OC(=O)—NR'— group, where R' and R" are as defined herein.

A "thiocarbamyl" or "thiocarbamate" group refers to an —OC(=S)—NR'R" group or an R"OC(=S)NR'— group, where R' and R" are as defined herein.

An "amino" group refers to an —NR'R" group where R' and R" are as defined herein.

An "amido" group refers to a —C(=O)—NR'R" group or a R'C(=O)—NR" group, where R' and R" are as defined herein.

A "nitro" group refers to an —NO$_2$ group.

A "cyano" group refers to a —C≡N group.

The term "phosphonyl" describes a —O—P(=O)(OR')(OR") group, with R' and R" as defined hereinabove.

The term "phosphinyl" describes a —PR'R" group, with R' and R" as defined hereinabove.

Preferably, n and m are each 0. More preferably, each of $R_1$, $R_4$, $R_5$ and $R_8$ is hydrogen or alkyl. More preferably, each of $R_1$, $R_4$, $R_5$ and $R_8$ is hydrogen.

The presently most preferred compound according to the present embodiments has the general Formula I above, wherein n and m are each 0 and each of $R_1$-$R_8$ is hydrogen. The preparation and analytical data of this compound is detailed in Example 1 in the Examples section that follows. This compound is referred to hereinafter as SAS.

The compounds of the present embodiments are typically prepared by reacting substantially equimolar amounts of a tellurium tetralkoxide and tartaric acid. These materials are combined in the presence of a water-free organic solvent, such as dried ethanol, dimethyl sulfoxide, i-propanol, and the like. Generally, the reaction may take place at ambient conditions, but, if desired, higher or lower temperatures and higher or lower pressures may be utilized.

Certain of the tellurium tetralkoxide compounds are known, and others may be prepared according to the method of Mehorta et al., [*J. Indian Chem. Soc.* 42: 1 (1965)], which is incorporated by reference.

The compounds described herein can further be in the form of pharmaceutically acceptable salts thereof. The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

The compounds of the present invention may be used in the treatment of pathologies associated with defects in the cell death pathway. These pathologies include inflammatory, autoimmune and neurodegenerative diseases, various forms of cancer, and developmental defects.

As discussed in the Background section hereinabove, it is known that in apoptotic responses, the family of cysteine proteases operates in a cascade mechanism, involving first initiators, then effectors. It has been found recently that ICE also requires "initiators", in particular, caspase-11 and -4, in order to become active (*Ann. Rev. Immunol.* 17: 781-828, 1999). Inhibition of IL-18 and IL-1β maturation in vitro and in vivo by AS101 may be due not only to its effect on caspase-1, but also partly due to its effect on other caspases which are required for the recruitment of ICE.

As described in the Examples section below, a representative compound according to the present embodiments, was prepared (see, Example 1). As shown in Example 2, it was unexpectedly found that the compounds of the present invention are ICE-inhibitors. They also inhibit the activity of two known substrates for ICE: IL-18 and IL-1β (see, Example 3). ICE inhibitors and their activities are described in U.S. Pat. Nos. 6,531,474 and 6,716,818, which are incorporated by reference.

The compound of Example 1 was tested for its inhibitory activity towards a member of the cysteine protease family, caspase-1 (ICE-Interleukin-1 β converting enzyme). The enzymatic reaction was carried out with caspase-1 specific calorimetric substrate, AC-YVAD-pNA, and in the absence or the presence of the tellurium compound of example 1 at different concentrations. The enzyme activity was tested for 1 hour and measured at 405 nm.

Figure 3:
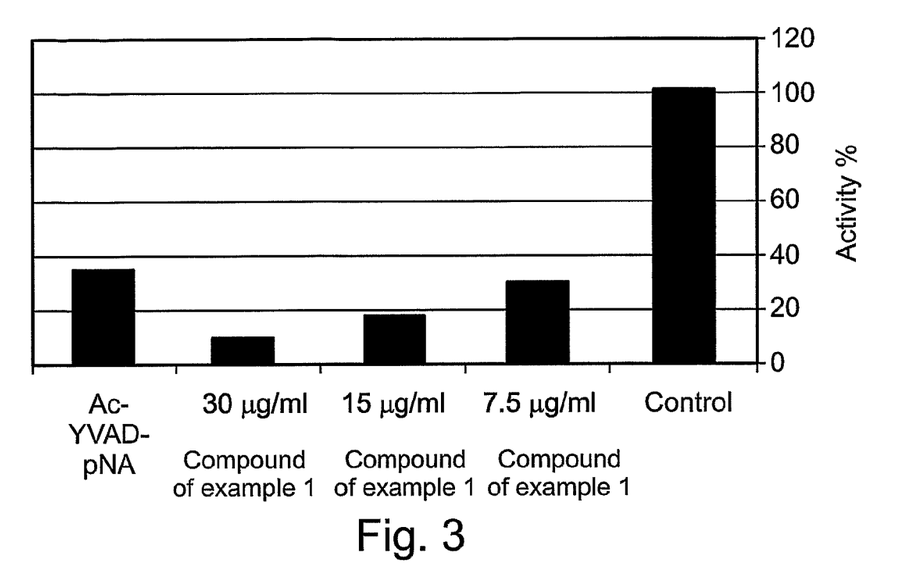
FIG. 3 is a bar graph demonstrating the inhibition of caspase-1 in an enzymatic reaction by the compound described in Example 1.

FIG. 3 shows the direct inhibition of ICE activity by the compound of Example 1 in a substrate specific enzymatic assay that demonstrates that the compound of Example 1 inhibits caspase-1 activity. 0 μM in the graph represents enzyme activity in the absence of the compound of Example 1, as a positive control. A caspase-1 specific inhibitor (AC-YVAD-p-NA) was added at the concentration of 0.1 μM as an internal control for the assay. The results, as presented in FIG. 3, expressed as percentage of residual enzymatic activity, show that the compound of Example 1 can directly, in a concentration dependent manner, inhibit ICE activity.

Figure 4:
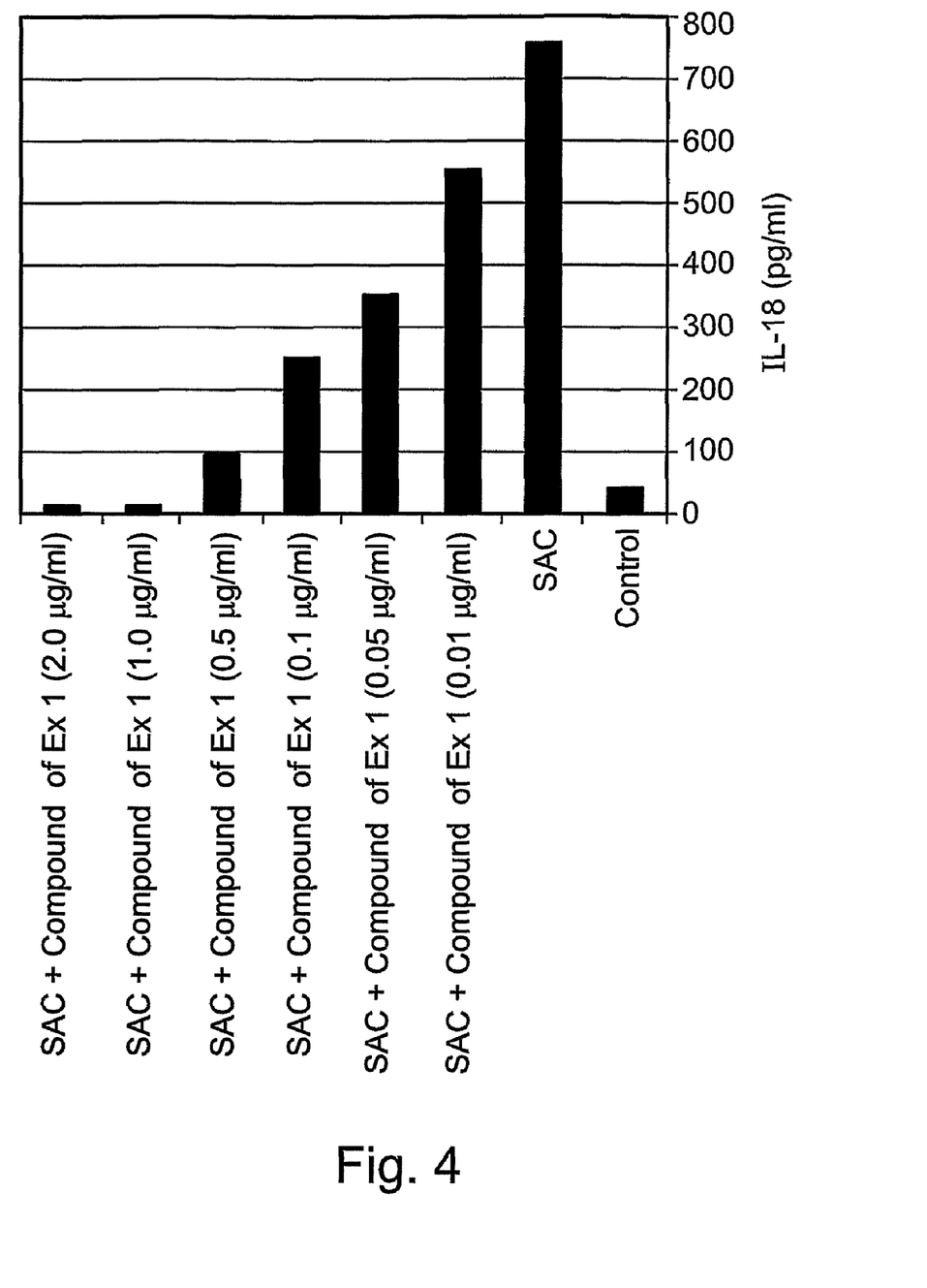
FIG. 4 is a graph demonstrating the inhibition of *Staphylococcus aureus*, Cowan strain, (SAC) induced secretion of IL-18 by the compound described in Example 1.

Following the direct inhibition of caspase-1 activity, it was determined that the compound of Example 1 is capable of inhibiting two of ICE's substrates: IL-18 and IL-1β (see, Example 3 in the Examples section that follows). SAC was used as a bacterial antigen, which is capable of stimulating PMBC to produce and secrete these two highly active inflammatory cytokines. Treatment with the compound of Example 1 in a concentration dependent manner was found to decrease SAC-induced secretion levels of IL-18 (see, FIG. 4) and IL-1β (see, FIG. 5) after 24 hours. The decrease in IL-18 and IL-1β secretion was significant, starting form 0.5 to 1 μg/ml (p<0.05) and 1.5 to 2 μg/ml (p<0.01). FIG. 4 illustrates this inhibitory effect of the tellurium compound of Example 1 on the secretion of cytokines.

The data presented herein suggest that SAS (a representative compound according to the present embodiments described in Example 1, as well as related tellurium-containing compounds, may contribute a significant role in balancing the immune response in many pathophysiological conditions, via inhibition of the caspase-1 (ICE) enzyme.

The present invention therefore provides a method of treating or preventing a condition in which inhibition of interleukin-1β-converting enzyme is beneficial, comprising administering to a subject in need thereof a therapeutically effective amount of a tellurium-containing compound of general formula I.

Conditions in which inhibition of interleukin-1β-converting enzyme is beneficial include, without limitation, IL-1 mediated disease, an inflammatory disease (such as, for example, septic shock, septicemia, adult respiratory distress syndrome, arthritis, cholangitis, colitis, encephalitis, hepatitis, pancreatitis and reperfusion injury), an autoimmune disease (such as, for example, psoriasis, rheumatoid arthritis, systemic lupus erythematosus, scleroderma, chronic thyroiditis, Graves' disease, autoimmune gastritis, insulin-dependent diabetes mellitus, autoimmune hemolytic anemia, autoimmune neutropenia, throbocytopenia, chronic active hepatitis, myasthenia gravis and multiple sclerosis), an ischemic disease (such as, for example, cerebral ischemia, myocardial ischemia, myocardial infarction, stroke, ischemic kidney disease; an immune based diseases, and hypersensitivity), a destructive bone disorder, a proliferative disorder, an infectious disease, a neurodegenerative disease (such as, for example, amyotrophic lateral sclerosis, Alzheimer's disease, Parkinson's disease, and primary lateral sclerosis), a disease associated with cell death, an excess dietary alcohol intake disease, retinal disorders, uveitis, inflammatory peritonitis, osteoarthritis, pancreatitis, asthma, glomerulonephritis, diabetes, inflammatory bowel disease, Crohn's disease, atopic dermatitis, scarring, graft vs host disease, organ transplant rejection, organ apoptosis after burn injury, osteoporosis, leukemia and related disorders, myelodysplastic syndrome, multiple myeloma-related bone disorder, acute myelogenous leukemia, chronic myelogenous leukemia, metastatic melanoma, Kaposi's sarcoma, multiple myeloma, haemorrhagic shock, sepsis, burns, Shigellosis, Huntington's disease, Kennedy's disease, prion disease, epilepsy, acute and chronic heart disease, myocardial infarction, congestive heart failure, atherosclerosis, coronary artery bypass graft, spinal muscular atrophy, HIV-related encephalitis, aging, neurological damage due to stroke, traumatic brain injury, spinal cord injury, yellow fever, dengue fever, Japanese encephalitis, liver disease, renal disease, polycystic kidney disease, *H. pylori*-associated gastric and duodenal ulcer disease, HIV infection, tuberculosis, an immunotherapy for the treatment of various forms of cancer, organ failure, meningitis and a complication associated with coronary artery bypass grafts.

The present invention further provides a method of treating or preventing obesity, comprising administering a therapeutically effective amount of the compound of Formula I.

The effect of the compounds described herein in preventing weight gain was also studied, as described in Example 4. It was found that the compound of Example 1 prevents weight gain when given intraperitoneally (ip) to ob/ob mice.

The effect of the compound of Example 1 was investigated in vivo, on body and fat composition in mice under standard diet. Mice treated with the compound of Example 1 every other day for 10 weeks gained significantly less body weight than untreated mice under a standard diet (see, FIG. 6).

In summary, the novel compounds described herein are useful for treating obesity, and related diseases (e.g., diabetes).

The compounds of the invention may be administered orally, alone for the treatment of obesity and/or type 2 diabetes or in combination with insulin or other antihyperglycemic drugs such as thiazolidinedione derivatives. If administered in combination with insulin, it may be possible to reduce the patients normal dose of insulin. For example, EP 749751 (which is incorporated herein by reference) teaches pharmaceutical compositions comprising an insulin sensitivity enhancer, which could be a thiazolidinedione compound, in combination with other antidiabetics. More specifically, EP 749751 teaches that the preferred insulin sensitivity enhancer is pioglitazone, which can be combined with other antidiabetics such as metformin, phenformin or buformin, trolitazone and metformin. Other combinations of antihyperglycemic drugs and thiazolidinedione derivatives can be found in U.S. Pat. Nos. 6,524,621; 6,475,521; 6,451,342 and 6,153,632 and PCT patent applications WO 01/3594 and WO 01/3594, which are incorporated herein by reference. The dose for the other antihyperglycemic drugs may be the known dose for the particular other antihyperglycemic drug.

The compounds of the present invention may be used for the treatment of conditions which have previously been described as amenable to treatment with ammonium trichloro (dioxyethylene-O,O')tellurate (AS101). Many of those conditions are described in U.S. Pat. Nos. 4,752,614; 4,761,490; 4,764,461; and 4,929,739, which are incorporated herein by reference. These include use as an adjuvant for enhancing the immune response of a subject to an immunoeffector, for example via induction of interleukin-12; for treatment of alopecia, and as a neuroprotective agent, for example in the treatment and prevention of neurodegenerative processes caused by trauma.

The tellurium compound is administered in a therapeutically effective amount. The term "therapeutically effective amount" or "pharmaceutically effective amount" denotes that dose of an active ingredient or a composition comprising the active ingredient that will provide the therapeutic effect for which the active ingredient is indicated. Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art. Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The exact formulation, route of administration and dosage can be chosen by the individual physician in view of the patient's condition. [See e.g., Fingl, et al., (1975) "The Pharmacological Basis of Therapeutics", Ch. 1 p. 1].

In any of the different embodiments of the method of the present invention, the tellurium-containing compounds described herein can be provided to a subject either per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to the subject treated.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered compound. As used herein, the term "carrier" refers to a diluent, adjuvant, excipient, or vehicle with which the therapeutic is administered.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutically acceptable carriers or diluents may be, for example, binders, (e.g., syrup, gum Arabic, gelatin, sorbitol, tragacanth, polyvinylpyrrolidone, etc), excipients (e.g., lactose, sucrose, corn starch, sorbitol), lubricants (e.g., magnesium stearate, talc, polyethylene glycol, silica, etc.), disintegrants (e.g. microcrystalline cellulose, potato starch, etc.), wetting agents (e.g. sodium lauryl sulfate, etc.), and the like. These pharmaceutical preparations may be in the form of a solid preparation such as tablets, capsules, powders, etc., or in the form of a liquid preparation such as solution, suspension, emulsion, etc., when administered orally. When administered parenterally, the pharmaceutical preparations may be in the form of a suppository, an injection or an intravenous drip, a physiological salt solution, and so on.

Therapeutic application of SAS and other tellurium compounds, can be contemplated to be accomplished by any suitable therapeutic method and technique presently or prospectively known to those skilled in the art. The tellurium compound may be administered in a variety of forms. These include orally, parenterally, rectally, nasally, topically or via inhalation. The parenteral route of administration may be intravenous, subcutaneous, intramuscular, etc.

In general, the composition of the subject invention will be formulated such that an effective amount of bioactive tellurium compound is combined with a suitable carrier in order to facilitate effective administration of the composition. The oral administration may be as a solid dosage form i.e. tablet with conventional excipients such as lactose, microcrystalline cellulose and the like.

It has been found that the tellurium compounds useful in the practice of the invention will hydrolyze in the presence of water. These hydrolyzed compositions are active in vivo and in vitro although the hydrolyzed compositions eventually decompose. For this reason, it is recommended that the compositions be freshly prepared or administered orally in the dry form. Preferably, the compounds should be kept under anhydrous conditions until just prior to being used.

Dosages can be titrated to the individual patient. The dose of SAS or a pharmaceutically acceptable salt thereof varies depending on the exact formulation, route of administration, ages, weights and condition of individual patients, or the severity of the disease.

When administering systemically, a therapeutically effective amount of the tellurium-containing compounds described herein may range, for example, from about 0.01 mg/m$^2$/day to about 20.0 mg/m$^2$/day and thus can be for example, 0.01 mg/m$^2$/day, 0.02 mg/m$^2$/day, 0.03 mg/m$^2$/day, 0.04 mg/m$^2$/day, 0.05 mg/m$^2$/day, 0.1 mg/m$^2$/day, 1 mg/m$^2$/day, 2 mg/m$^2$/day, 3 mg/m$^2$/day, 4 mg/m$^2$/day, 5 mg/m$^2$/day, 6 mg/m$^2$/day, 7 mg/m$^2$/day, 8 mg/m$^2$/day, 9 mg/m$^2$/day, 10 mg/m$^2$/day, 15 mg/m$^2$/day and even 20 mg/m$^2$/day.

Preferably, when administered parenterally, the therapeutically effective amount is 0.01 mg/m$^2$/day and higher and thus can be, for example, 0.01 mg/m$^2$/day, 0.05 mg/m$^2$/day, 0.1 mg/m$^2$/day, 0.2 mg/m$^2$/day, 0.5 mg/m$^2$/day, 0.6 mg/m$^2$/day, 0.7 mg/m$^2$/day, 0.8 mg/m$^2$/day, 0.9 mg/m$^2$/day, 1.0 mg/m$^2$/day, 2.0 mg/m$^2$/day, 3.0 mg/m$^2$/day, 4.0 mg/m$^2$/day, 5.0 mg/m$^2$/day, and up to 20.0 mg/m$^2$/day. Preferably, the parenteral dose when given intramuscularly, intravenously, or otherwise, is from about 1 mg/m$^2$/day to about 10 mg/m$^2$/day.

When administered to humans, and depending on the age and weight of the treated subject, the compounds of the present invention may be administered orally at doses of from about 0.1 mg to about 200, and preferably of from about 1 mg to about 150 mg per day, preferably in divided doses.

The compounds may be administered topically, preferably as a pharmaceutical composition, as detailed hereinbelow, formulated for topical application. When administered topically, preferably a composition having a concentration of from about 0.02 weight percents to about 50 weight percents in a suitable ointment or cream base.

Depending on the severity and responsiveness of the condition to be treated, dosing can be of a single or a plurality of administrations, with course of treatment lasting from several days to several weeks or until cure is effected or diminution of the disease state is achieved.

The method according to this aspect of the present invention can further comprise, in addition to administering the tellurium-containing compounds described above, co-administration of an additional active agent. The co-administration can be effected prior to, concomitant with or subsequent to the administration of the tellurium-containing compound. The additional active agent is used for providing an additive beneficial effect in terms of the ailment being treated, conditions associated with the ailment being treated or other parameters such as psychological effects and prophylactic effects.

Hence, exemplary additional active agents according to this embodiment of present invention include, without limitation, one or more, or any combination of an antibiotic agent, an anti-diabetic agent, an antihyperglemic agent, an antimicrobial agent, an anti-obesity agent, an anesthetic agent, a suitable anti-oxidant, a chemotherapeutic agent, an antidepressant, an anti-histamine, a vitamin, and a hormone.

Representative examples of non-steroidal anti-inflammatory agents that are usable in this context of the present invention include, without limitation, oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the pharmaceutically acceptable salts and esters of these agents.

Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluorometholone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Non-limiting examples of anesthetic drugs that are suitable for use in the context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of antineoplastic agents usable in the context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

Non-limiting examples of antidepressants usable in the context of the present invention include norepinephrine-reuptake inhibitors ("NRIs"), selective-serotonin-reuptake inhibitors (SSRIs), monoamine-oxidase inhibitors (MAOIs), serotonin-and-noradrenaline-reuptake inhibitors ("SNFIs), corticotropin-releasing factor (CRF) antagonists, α-adreno-receptor antagonists, NK1-receptor antagonists, 5-HT$_{1A}$-receptor agonist, antagonists, and partial agonists and atypical antidepressants, as well as norepinephrine-reuptake inhibitors such as, but are not limited to amitriptyline, desmethylamitriptyline, clomipramine, doxepin, imipramine, imipramine-oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norcloliparamine, noxiptilin, opipramol, perlapine, pizotyline, propizepine, quinupramine, reboxetine, tianeptine, and serotonin-reuptake inhibitors such as, but are not limited to, binedaline, m-chloropiperzine, citalopram, duloxetine, etoperidone, femoxetine, fluoxetine, fluvoxamine, indalpine, indeloxazine, milnacipran, nefazodone, oxaflazone, paroxetine, prolintane, ritanserin, sertraline, tandospirone, venlafaxine and zimeldine.

Non-limiting examples of vitamins usable in the context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin B$_3$ (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of antihistamines usable in the context of the present invention include chlorpheniramine, brompheniramine, dexchlorpheniramine, tripolidine, clemastine, diphenhydramine, promethazine, piperazines, piperidines, astemizole, loratadine and terfenadine.

Suitable hormones for use in the context of the present invention include, for example, androgenic compounds and progestin compounds.

Representative examples of androgenic compounds include, without limitation, methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing.

Representative examples of progestin compounds include, without limitation, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlornadinone acetate, megestrol acetate, norgestimate, norgestrel, desogrestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, fluorogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

The compounds described hereincan be utilized in any of the methods described herein, either per se or as a part of a pharmaceutical composition, which further comprises a pharmaceutically acceptable carrier.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

Pharmaceutical compositions may also be prepared according to the procedures set forth in the above-identified patents. Suitable pharmaceutical carriers are well known and are described in Remington 20th Ed., Lippincott, Williams & Wilkins, Balt. Md (2000), Chapter 45, which is incorporated by reference.

For injection, the active ingredients of the invention may be formulated in aqueous solutions, preferably in physiologically compatible buffers such as Hank's solution, Ringer's solution, or physiological salt buffer.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared and placed in an appropriate container. The compositions are preferably identified in print, in or on the packaging material, for use in the treatment or prevention of a neurodegenerative process associated with trauma.

The compositions of the present invention may be packed or presented in any convenient way. For example, they may be packed in a tube, a bottle, or a pressurized container, using techniques well known to those skilled in the art and as set forth in reference works such as Remington's Pharmaceutical Science $15^{th}$ Ed. It is preferred that the packaging is done in such a way so as to minimize contact of the unused compositions with the environment, in order to minimize contamination of the compositions before and after the container is opened.

Compositions of the present invention may, if desired, be presented in a pack or dispenser device, such as an FDA approved kit, which may contain one or more unit dosage forms containing the active ingredient. The pack may, for example, comprise glass, plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Preparation of SAS-An Exemplary Bis-Tellurium Compound

Tellurium tetra-isopropoxide was prepared according to the procedure set forth by Mehrota et al., [*J. Indian Chem, Soc.*, 1965, 42, 1].

Tartaric acid (0.3 gram) was dissolved in 3.00 ml of dried ethanol, which was dried by flashing dry argon gas into the reaction flask. To the dissolved tartartic acid, 0.5 ml of tellurium tetra-isopropoxide was added in the presence of dry argon gas. The mixture was stirred at room temperature (25° C.) for 24 hours and the compound obtained from the reaction of tartaric acid and tellurium tetra-isopropoxide was precipitated. Centrifugation followed by decantation was used to separate the solid compound. The compound was washed with dried ethanol and dried by vacuum (0.1 mm/Hg, at 25° C. for 24 hours).

Melting point (mp) was 220° C.(d).

The elemental analysis for $C_{10}H_{10}O_3Te_2$ was: calcu: C, 20.28%; H, 1.53%; Te: 43.08%. found: C, 20.44%; H, 1.83%; Te: 44.51%.

Figure 1:
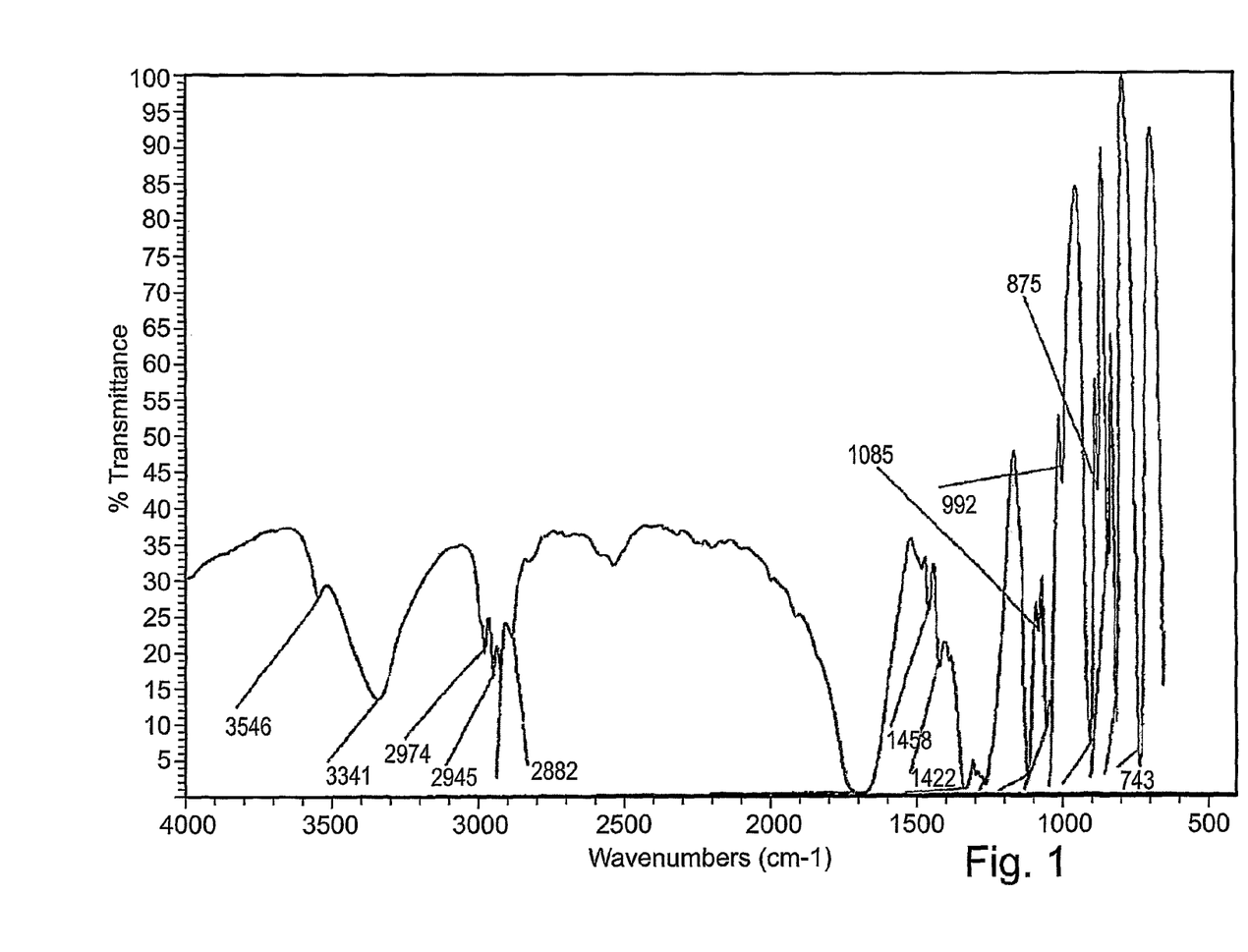
FIG. 1 presents the IR spectrum of the compound described in Example 1 being complexed with four molecules of DMSO (a 3% sample in KBr)

The IR spectrum of the obtained product is shown in FIG. 1.

$^1$H-NMR ($D_6$-DMSO): δ=3.344 ($H_2O$), 4.696 (SAS) ppm.
$^{13}$C-NMR ($D_6$-DMSO): δ=76.62, 273.89 ppm.
$^{125}$Te-NMR ($D_6$-DMSO): δ=1463.06 ppm.

Figure 2:
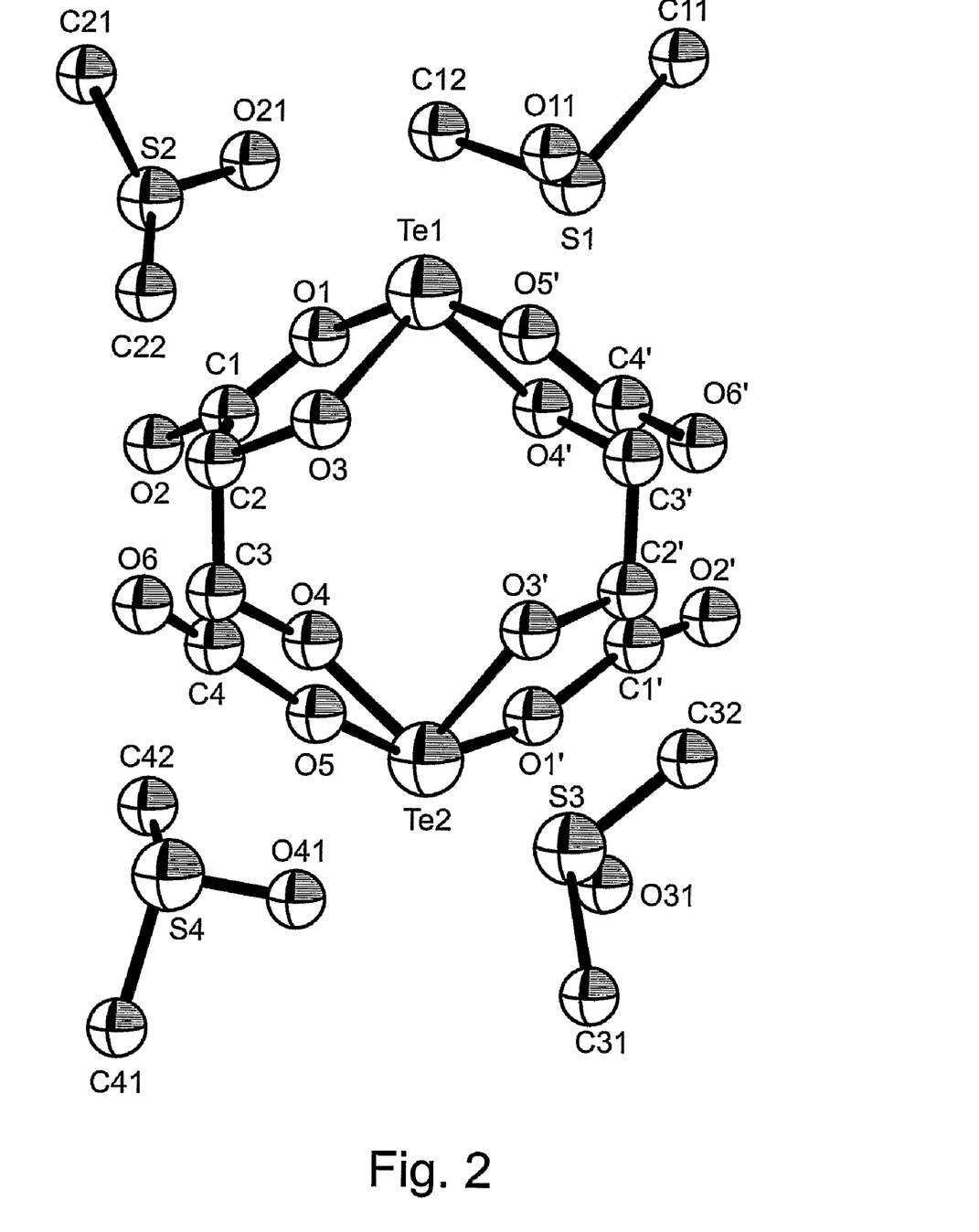
FIG. 2 presents a diagram of the structure of the compound described in Example 1 showing four molecules of dimethyl sulfoxide in association with a single crystal.

The crystallographic data of the obtained product are presented in Tables 1-3 below and is further shown in FIG. 2.

The positional parameters for (041) Sigal P21 are presented in Table 1 below.

The intramolecular distances involving the non-hydrogen atoms are presented in Table 2 (standard deviation given in parenthesis to least significant figure).

The intramolecular bond angles involving the non-hydrogen atoms (angles in degrees; Standard deviation given in least significant figure in parenthesis) are presented in Table 3.

TABLE 1

| atom | x | y | z |
|---|---|---|---|
| Te(1) | 0.1488(2) | 0.200 | 0.4804(2) |
| Te(2) | 0.1897(2) | 0.1891(2) | 1.0213(2) |
| S(1) | 0.070(1) | 0.4002(5) | 0.363(1) |
| S(2) | 0.375(2) | 0.0239(7) | 0.358(1) |
| S(3) | −0.070(2) | 0.0527(7) | 1.129(1) |
| S(4) | 0.561(1) | 0.2384(6) | 1.155(1) |
| O(1) | 0.335(2) | 0.273(1) | 0.529(2) |
| O(1') | 0.116(3) | 0.300(1) | 0.981(3) |
| O(2) | 0.546(3) | 0.283(1) | 0.657(2) |
| O(2') | −0.068(3) | 0.370(2) | 0.871(3) |
| O(3) | 0.256(2) | 0.137(1) | 0.620(2) |
| O(3') | 0.034(2) | 0.169(1) | 0.878(2) |
| O(4) | 0.340(2) | 0.221(1) | 0.889(2) |
| O(4') | 0.048(2) | 0.2634(9) | 0.620(2) |
| O(5) | 0.258(3) | 0.078(1) | 0.966(2) |
| O(5') | −0.025(2) | 0.126(1) | 0.528(2) |
| O(6) | 0.428(3) | 0.020(1) | 0.829(2) |
| O(6') | −0.234(3) | 0.118(1) | 0.655(2) |
| O(11) | 0.047(2) | 0.313(1) | 0.328(2) |
| O(21) | 0.289(5) | 0.089(2) | 0.320(4) |
| O(31) | −0.050(3) | 0.138(2) | 1.163(3) |
| O(41) | 0.403(4) | 0.245(2) | 1.179(3) |
| C(l) | 0.434(4) | 0.248(2) | 0.620(3) |
| C(l') | −0.006(4) | 0.308(2) | 0.901(4) |
| C(2) | 0.404(4) | 0.168(2) | 0.672(3) |
| C(2') | −0.055(4) | 0.229(2) | 0.832(3) |
| C(3) | 0.420(3) | 0.160(1) | 0.821(3) |
| C(3') | −0.084(3) | 0.233(2) | 0.679(3) |
| C(4) | 0.373(4) | 0.078(2) | 0.880(4) |
| C(4') | −0.124(3) | 0.151(1) | 0.616(3) |
| C(11) | −0.044(4) | 0.452(2) | 0.232(4) |
| C(12) | 0.251(5) | 0.422(2) | 0.308(4) |
| C(21) | 0.399(5) | −0.038(2) | 0.209(4) |
| C(22) | 0.350(8) | −0.048(5) | 0.461(8) |
| C(31) | −0.128(5) | 0.004(2) | 1.290(4) |
| C(32) | −0.228(6) | 0.042(3) | 1.019(5) |
| C(41) | 0.655(4) | 0.245(2) | 1.334(5) |
| C(42) | 0.625(5) | 0.323(3) | 1.082(5) |
| H(2) | 0.479 | 0.135 | 0.635 |
| H(2') | −0.151 | 0.218 | 0.868 |
| H(3) | 0.525 | 0.166 | 0.847 |
| H(3') | −0.167 | 0.268 | 0.659 |

TABLE 2

| atom | atom | distance(Å) |
|---|---|---|
| Te(1) | O(1) | 2.09(2) |
| Te(1) | O(3) | 1.91(2) |
| Te(1) | O(4') | 1.96(2) |
| Te(1) | O(5') | 2.05(2) |
| Te(2) | O(1') | 2.01(2) |
| Te(2) | O(3') | 1.91(2) |
| Te(2) | O(4) | 1.95(2) |
| Te(2) | O(5) | 2.05(2) |
| S(1) | O(11) | 1.53(2) |
| S(1) | C(11) | 1.79(4) |
| S(1) | C(12) | 1.74(4) |
| S(2) | O(21) | 1.38(4) |
| S(2) | C(21) | 1.79(4) |
| S(2) | C(22) | 1.58(8) |
| S(3) | O(31) | 1.49(3) |
| S(3) | C(31) | 1.83(4) |
| S(3) | C(32) | 1.71(5) |
| S(4) | O(41) | 1.43(3) |
| S(4) | C(41) | 1.85(4) |
| S(4) | C(42) | 1.70(5) |
| O(1) | C(1) | 1.27(3) |
| O(1') | C(1') | 1.29(3) |
| O(2) | C(1) | 1.18(3) |
| O(2') | C(1') | 1.21(4) |
| O(3) | C(2) | 1.47(4) |
| O(3') | C(2') | 1.34(3) |
| O(4) | C(3) | 1.43(3) |
| O(4') | C(3') | 1.41(3) |
| O(5) | C(4) | 1.33(4) |
| O(5') | C(4') | 1.31(4) |
| O(6) | C(4) | 1.21(4) |
| O(6') | C(4') | 1.19(3) |
| C(1) | C(2) | 1.48(4) |
| C(1') | C(2') | 1.54(4) |
| C(2) | C(3) | 1.42(4) |
| C(2') | C(3') | 1.47(4) |
| C(3) | C(4) | 1.55(4) |
| C(3') | C(4') | 1.54(3) |

TABLE 3

| atom | atom | atom | angle |
|---|---|---|---|
| O(1) | Te(1) | O(3) | 80.2(7) |
| O(1) | Te(1) | O(4') | 84.3(7) |
| O(1) | Te(1) | O(5') | 154.4(8) |
| O(3) | Te(1) | O(4') | 93.6(7) |
| O(3) | Te(1) | O(5') | 81.3(8) |
| O(4') | Te(1) | O(5') | 79.4(8) |
| O(1') | Te(2) | O(3') | 79.7(8) |
| O(1') | Te(2) | O(4) | 80.7(9) |
| O(1') | Te(2) | O(5) | 154.1(9) |
| O(3') | Te(2) | O(4) | 94.3(8) |
| O(3') | Te(2) | O(5) | 82.0(8) |
| O(4) | Te(2) | O(5) | 82.6(8) |
| O(11) | S(1) | C(11) | 106(2) |
| O(11) | S(1) | C(12) | 105(2) |
| O(11) | S(1) | C(12) | 100(2) |
| O(21) | S(2) | C(21) | 110(2) |
| O(21) | S(2) | C(22) | 133(4) |
| C(21) | S(2) | C(22) | 94(3) |
| O(31) | S(3) | C(31) | 107(2) |
| O(31) | S(3) | C(32) | 109(2) |
| C(31) | S(3) | C(32) | 102(2) |
| O(41) | S(4) | C(41) | 104(2) |
| O(41) | S(4) | C(42) | 110(2) |
| O(41) | S(4) | C(42) | 100(2) |
| Te(1) | O(1) | C(1) | 117(2) |
| Te(2) | O(1') | C(1') | 118(2) |
| Te(1) | O(3) | C(2) | 115(2) |
| Te(2) | O(3') | C(2') | 118(2) |
| Te(2) | O(4) | C(3) | 117(1) |
| Te(1) | O(4') | C(3') | 119(1) |
| Te(2) | O(5) | C(4) | 113(2) |
| Te(1) | O(5') | C(4') | 118(2) |
| O(1) | C(1) | O(2) | 125(3) |
| O(1) | C(1) | C(2) | 114(3) |
| O(2) | C(1) | C(2) | 121(3) |
| O(1') | C(1') | O(2') | 126(3) |
| O(1') | C 1') | C(2') | 111(3) |
| O(2') | C(1') | C(2') | 123(3) |
| O(3) | C(2) | C(1) | 113(3) |
| O(3) | C(2) | C(3) | 110(3) |
| C(1) | C(2) | C(3) | 115(2) |
| O(3') | C(2') | C(1') | 112(2) |
| O(3') | C(2') | C(3') | 115(3) |
| C(1') | C(2') | C(3') | 115(3) |
| O(4) | C(3) | C(2) | 110(2) |
| O(4) | C(3) | C(4) | 110(3) |
| C(2) | C(3) | C(4) | 116(3) |
| O(4') | C(3') | C(2') | 108.2 |
| 0(4') | C(3') | C(4') | 111(2) |
| C(2') | C(3') | C(4') | 112(2) |
| O(5) | C(4) | O(6) | 125(3) |
| O(5) | C(4) | C(3) | 116(3) |
| O(6) | C(4) | C(3) | 118.4 |
| O(5') | C(4') | O(6') | 128(3) |
| O(5') | C(4') | C(3') | 113(3) |
| O(6') | C(4') | C(3') | 118(3) |

The atom designator code (ADC) specifies the position of an atom in a crystal. The 5-digit number shown in the table is a composite of three one digit numbers and one two digit number: TA (1st digit)+TB (2nd digit)+TC (3rd digit)+SN (4th and 5th digit). TA, TB and TC are the crystal latice translation digits along cell edges a, b, and c. A translation digit of 5 indicates the origin unit cell. If TA=4, this indicates a translation of one unit cell length along the a axis from 1 to 9 and thus (+/−) 4 latice translations from the origin (TA=5, TB=5, TC=5) can be represented.

The SN or symmetry operator number refers to the number of the symmetry operator used to generate the coordinates of the target atom. A list of the symmetry operators relevant to this structure are given below.

For a given intermolecular contact, the first atom (origin atom) is located in the origin unit cell (TA=5, TB=5, TC=5) and its position can be generated using the identity operator (SN=1). Thus, the ADC for an origin atom is always ADC=55501. The position of the second atom (target atom) can be generated using the ADC and the coordinates of that atom in the parameter table. For example, an ADC of 47502 refers to the target atom moved through operator two, then translated −1 cell translations along the a axis, +2 cell translations along the b axis, and 0 cell translations along the c axis.

An ADC of 1 indicates an intermolecular contact between two fragments (i.e. cation and anion) that reside in the same asymmetric unit.

Symmetry Operators:

$$+X, +Y, +Z \quad (1)$$

$$-X, \tfrac{1}{2}+Y, -Z \quad (2)$$

Example 2

Inhibition of Caspase-1/Interleukin-β-Converting Enzyme

Cells: Human peripheral blood mononuclear cells (PBMC) were isolated from randomly selected healthy donors by Ficoll-Hypaque (Pharmacia, Piscataway, N.J.) density-gradient centrifugation. PBMC were adjusted to 2.5× $10^6$ cells/ml and cultured in enriched RPMI 1640 medium (Biological industries, Kibbutz Beit Haemek, Israel) with 10% Fetal Calf Serum (FCS) (Biological Industries) at 37° C. and 7% $CO_2$.

Reagents: The following bacterial antigens, antibodies and peptides were applied: heat-inactivated *Staphylococcus aureus* Cowan strain (SAC ($10^{-3}$ v/v; Calbiochem, Bad Homburg, Germany), Lipopolysaccharide [LPS (40-60 ng/ml, in vitro) and (0.5 mg/mouse, in vivo); *salmonella Enteritidis*, Sigma Aldrich, Rehovot, Israel), rCaspase-1 and specific inhibitor (Ac-YVAD-CHO) (Biomol and International Industries L.P. Canada). Caspase-1 calorimetric substrate (AC-YVAD-pNA) (Alexis Biochemicals, Inc. San Diego, Calif.). The compound of Example 1 was supplied by the Chemistry Department at Bar Ilan University, in a solution of PBS, pH 7.4 (Example 10 of U.S. Pat. No. 4,764,461, which is incorporated by reference) and maintained at 4° C.

In vitro studies: Cells were first treated with various concentrations of the compound of Example 1 (SAS) and after 1 hour SAC was added. After 24 hours, supernatants were collected and evaluated for cytokine content. Viability at the end of these experiments, as assessed by trypan blue exclusion method, was always found to be greater than 95%.

DTT (Dithiothreitol), which is present in the commercial enzyme solution, interacts with the compound of Example 1 and would thus interfere with the inhibition studies. Therefore removal of the DTT from the enzyme solution prior to the enzymatic assay was necessary. Gel permeation chromatography was carried out at 4° C. 50 µl solution of commercial activated rCaspase-1 was loaded on a 1×15 cm Sephadex G-15 column (Pharmacia), pre-equilibrated with assay buffer containing: 50 mM Hepes, 100 mM NaCl, 0.1% CHAPS, 1 mM EDTA, 10% Glycerol at pH 7.4, the enzyme was eluted with the same buffer (DEGASSED) at 0.5 ml/min and 500 µl fractions were collected. The enzyme-substrate reaction was measured continuously with 1 minute intervals for a total time of 1 hour at 30° C. and was read at 405 nm. The total volume of the reaction was 100 µl and contained as following: 50 µl rCaspase-1 (0.8 U/µl), 25 µl calorimetric substrate (Ac-YVAD-pNA, 200 µM), 25 µl of the compound of Example 1 at various concentration (2.550 µM, 5 µM, 10 µM) in assay buffer. Results are shown in FIG. 3.

Statistical analysis: Data are presented as mean ±SE. For comparisons of means of the various groups, the pair wise t test was used

Example 3

Inhibitory Effect of SAS on the Extracellular Levels of SAC Induced Secretion of Active IL-18 and IL-1β by PMBC The compound described in Example 1 (SAS) was delivered to the medium 1 hour before stimulation with SAC. Optimal concentration of SAC for cytokine secretion stimulation was $10^{-3}$ V/V (data not shown).

Figure 5:
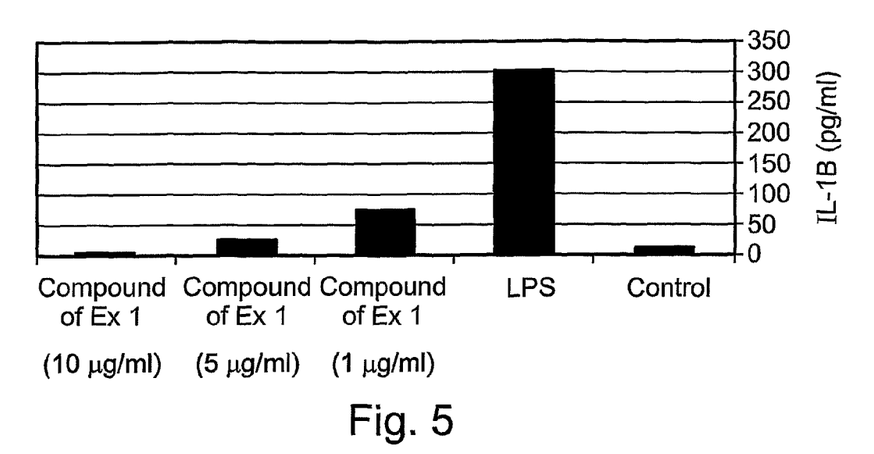
FIG. 5 is a graph demonstrating the inhibition of SAC induced secretion of IL-1β by PBMC due to the effect of the compound described in Example 1.

PBMC ($2.5 \times 10^6$ cells/ml) were treated with various concentration of the tellurium compound of Example 1 and after 1 hour were stimulated with SAC ($10^{-3}$ V/V). It was found that SAS decreased SAC-induced secretion levels of IL-18 (FIG. 4) and IL-1β (FIG. 5). Results as shown in FIGS. 4 and 5 represent means ±SE of three experiments **$p<0.05$ decrease vs SAC; *$p<0.01$ decrease vs SAC.

Example 4

Prevention of Weight Gain by SAS

Animal experiments were performed in accordance with approved institutional protocols and approved by the Institutional Animal Care and Use Committee.

Female ob/ob mice 7 weeks old were injected intraperitoneally (ip) with SAS (10 µg/ml in PBS) every other day. Control animals were injected every other day with PBS. Body weight was monitored on a daily basis.

It was found that weight gain was prevented in the SAS-treated mice.

Figure 6:
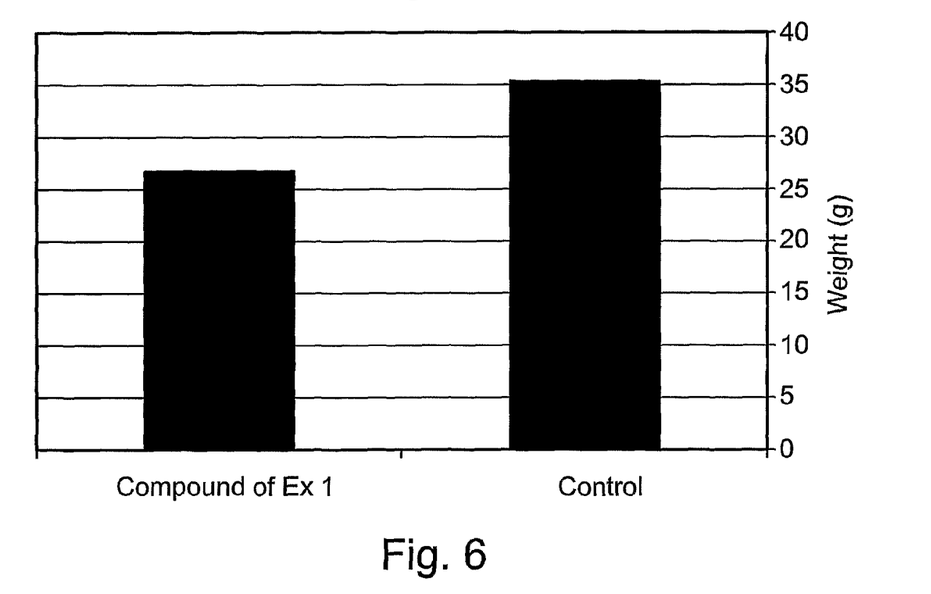
FIG. 6 is a bar graph demonstrating the effect of the compound described in Example 1 on weight gain in mice treated therewith, compared with control fed the same standard diet.

Additional results, presented in FIG. 6, show the effect of the compound of Example 1 on reducing/preventing weight gain in mice, as compared with non-treated mice fed with the same standard diet.

Example 5

Effect of SAS in Treatment of Hair Loss

A patient suffering from hair loss applies a spray containing 0.017% SAS in 20% propylene glycol, 20% water and 60% ethyl alcohol twice daily. The results are monitored at commencement of the study, after about 1 month, after about 3 months, and after about 6 months. Hair density, terminal hair density, and vellus hair density are analyzed, using the Dating Image DB image archiving system, and TichoScan software.

Example 6

Effect of SAS on IL-12 Production by Human Monocytes

Adherent Peripheral Blood Mononuclear Cells (PBMCs) from a tuberculin-negative healthy donor are incubated with SAS (0.87-3.5 µg/ml PBS) or *E. coli* lipopolysaccharide (LPS) (1 ng/ml PBS; Sigma) for 24 hours. Supernatants are collected after 28 hours for analysis of IL-12 production. Cell supernatants are determined using commercially available Enzyme-Linked Immunosorbent Assay (ELISA) kits (R&D Systems). Supernatants are tested for IL-12p40 by ELISA kit (Endogene).

Example 7

Effects of SAS on IL-12 p40 Production by Murine Bone Marrow-Derived Dendritic Cells Murine bone marrow-derived dendritic cells (DC) are prepared by culturing bone marrow cells from the femur and tibia of mice in RPMI medium supplemented with 10% supernatant from a granulocyte-monocyte colony-stimulating factor-secreting cell line.

On day 7 of culture, cells are collected, washed, and resuspended in RPMI medium. DC ($10^6$ cells/ml) are cultured with SAS (0.87-17.5 µg/ml) or with CpG. Supernatants are collected after 24 hours for analysis of IL-12 p40 production. Cell supernatants are determined using commercially available ELISA kits (R&D Systems).

Example 8

Effects of SAS on Serum Antibody Responses to KLH

Serum was obtained from mice immunized with depyrogenated keyhole limpet hemocyanin (KLM) (5 µg; Calbiochem, La Jolla, Calif.); or with KLH plus phosphorothioate-stabilized oligodeoxynucleotide-containing CpG motifs (CpG-ODN) (5'-GCTAGACGTTAGCGT-3'), synthesized by Sigma-Genosys Ltd., Cambridge, United Kingdom; or with KLH, plus CpG, plus SAS (17.5 µg/ml PBS); or with Dulbecco's PBS (Sigma, Poole, United Kingdom) in a final volume of 50 µl.

On day 7 after the first or second immunization, mice are sacrificed by cervical dislocation, and serum and popliteal lymph nodes collected in the presence or absence of SAS (17.5 µg/ml). Titers of KLH-specific IgG1 and IgG2a in the serum of immunized mice are determined by ELISA, and analysed for the presence of antibody subclasses IgGb1 and IgG2a.

Example 9

Assessment of the Neuroprotective Effects of SAS

To assess the neuroprotective effects of SAS, PC12 cells are maintained in Dulbecco's modified Eagle's medium supplemented with 8% heat inactivated horse serum, 8% heat inactivated fetal bovine serum, glutamine (5 mM) and 50 µg/ml gentamycin at 37° C.

PC12 cells are washed in serum-free medium, resuspended to $1-5\times10^6$ cells/ml. After 24 hours of incubation at 37° C. in culture, the cells are supplemented with 3 ml of medium (RPMI 1640 containing 10% FCS, 2% glutamine and 1 mg/ml G418 (Life Technologies, Inc.). After another 24 hours, cells are resuspended and maintained in the selection medium. After 3-4 weeks in selective medium, transfected cells are analyzed for via Western blotting. Results are expressed as percent p21 as compared to the negative (no drug) control.

The ras Asn-17 gene is then cloned into a mammalian expression vector. Transfection of PC12 cells with the plasmid DNA is performed with the calcium phosphate precipitation technique.

PC12 cell extracts (20 µg/lane of protein) boiled under reducing conditions, are subjected to electrophoresis on 7.5 and 12.5% polyacrylamide gels and electro-transferred to nitrocellulose membranes. The membrane is blocked for one hour with 10% powdered milk in 0.2% Tween 20, Tris-buffered saline, and then incubated with the appropriate specific detecting antibodies. Immunoreactive proteins are detected with horseradish peroxidase-conjugated secondary antibodies (Amersham, Arlington Heights, Ill.) and a chemiluminescence reagent. For immunoprecipitation studies, immune complexes are precipitated with Protein A-Sepharose (Pharmacia) and, following electrophoresis, blotted with anti-phosphoserine or anti-phosphotyrosine antibodies.

Endogenous JNK and erk are immunoprecipitated from cell lysates with specific antibodies and their activities measured by using $P^{32}$ ATP and glutathione s-transferase (GST) e-jun or myelin basic protein (MPB) respectively, as the substrate. Samples are run on SDS-polyacrylamide gel electrophoresis gels and subjected to PhosphorImager analysis.

Example 10

Activation of the Ras Superfamily GTPases

The effect of SAS on signaling pathways that are controlled by Ras superfamily GTPases is screened by parallel analysis of the activation of the Ras family GTPases and their effectors. The primary methods used for studying activation of different Ras superfamily GTPases are: (a) pull down of activated Ras superfamily GTPases from cell lysates, by binding of the specific recombinant purified effector GTPase binding domains to the activated GTP bound form. Subsequent to the pull down of the activated GTPases, the proteins are detected and quantified by western blotting; (b) activation of GTPases effectors such as Raf or RAC, by reporter gene assays; and (c) direct immunoprecipitation kinase assays.

Example 11

Detection of Apoptosis

The percentage of cells undergoing apoptosis is quantitatively determined using an Apoptosis Detection kit, on the basis of their ability to bind annexin V and exclude iodide, and also by an in situ cell detection kit incorporating HTC labeling and TUNEL.

Example 12

Cell Cycle Distribution

Cell cycle distribution studies is performed as previously described. Cells are trypsinyzed and suspended for 10 minutes at room temperature at 1.106/ml buffer containing 1 mg/ml RNAse, 1% NP-40, 10 µg/ml propidium iodide and 0.1% sodium citrate. Propidium iodide fluorescence is measured using a FACStar plus flow cytometer equipped with an air-cooled argon laser delivering 15 mW of light at 488 nM. The red fluorescence from 1.104 cells from each sample is collected through a 610 nm bandpass filter.

Example 13

Evaluation of the Therapeutic Use of SAS Utilizing Rat Spinal Cord Injury Model

Twenty rats are divided into 4 treatment groups (control, SAS 15; 20; 30 µg). Experimental spinal cord injury (SCI) is induced via weight-drop contusion models that result in significant locomotor deficits, including lack of coordination and trunk stability. SAS is applied topically to the damaged area and rats were treated for 21 days with SAS administrated i.v. At the end of the first week following SCI, and on days 14 and 21, recovery was determined using Basso, Beattie and Bresnahan (BBB) locomotor scale score.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A tellurium-containing compound having the general formula I:

Formula I wherein:

each of m and n is independently an integer from 0 to 3; and each of $R_1$-$R_8$ is independently selected from the group consisting of hydrogen, hydroxyalkyl, hydroxy, thiohydroxy, alkyl, alkenyl, alkynyl, alkoxy, thioalkoxy, halogen, haloalkyl, carboxy, C(O)R', wherein R' is selected from the from group consisting of hydrogen, alkyl, alkenyl, cycloalkyl, aryl, heteroaryl, or a heteroalicyclic group, alkylcarbonylalkyl, carboxyalkyl, amido, cyano, N-monoalkylamidoalkyl, N,N-dialkylamidoalkyl, cyanoalkyl, alkoxyalkyl, carbamyl, cycloalkyl, heteroalicyclic, sulfonyl, sulfinyl, sulfate, amine, aryl, heteroaryl, phosphate, phosphonate and sulfoneamido.

2. The compound of claim 1, wherein n and m are each 0.

3. The compound of claim 2, wherein each of $R_1$, $R_4$, $R_5$ and $R_8$ is hydrogen.

4. The compound of claim 1, wherein each of $R_1$-$R_8$ is independently selected from the group consisting of hydrogen, hydroxy, thiohydroxy, halogen and cyano.

5. A pharmaceutical composition comprising the compound of claim 1 and a pharmaceutically acceptable carrier.

6. A pharmaceutical composition comprising the compound of claim 3 and a pharmaceutically acceptable carrier.

* * * * *